(12) United States Patent
Mizukami

(10) Patent No.: US 11,141,043 B2
(45) Date of Patent: Oct. 12, 2021

(54) SIGNAL PROCESSING DEVICE AND MEDICAL OBSERVATION SYSTEM

(71) Applicant: Sony Olympus Medical Solutions Inc., Tokyo (JP)

(72) Inventor: Aki Mizukami, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 92 days.

(21) Appl. No.: 15/567,660

(22) PCT Filed: Feb. 22, 2016

(86) PCT No.: PCT/JP2016/055098
§ 371 (c)(1),
(2) Date: Oct. 19, 2017

(87) PCT Pub. No.: WO2016/185746
PCT Pub. Date: Nov. 24, 2016

(65) Prior Publication Data
US 2018/0110399 A1    Apr. 26, 2018

(30) Foreign Application Priority Data

May 20, 2015    (JP) .............................. JP2015-103137

(51) Int. Cl.
*A61B 1/00*    (2006.01)
*A61B 1/04*    (2006.01)
*A61B 1/05*    (2006.01)

(52) U.S. Cl.
CPC ........ *A61B 1/00009* (2013.01); *A61B 1/0002* (2013.01); *A61B 1/00006* (2013.01);
(Continued)

(58) Field of Classification Search
CPC . A61B 1/00009; A61B 1/053; A61B 1/00045; A61B 1/00006; A61B 1/0002; A61B 1/04
See application file for complete search history.

(56) References Cited

U.S. PATENT DOCUMENTS

| 6,526,098 B1 * | 2/2003 | Kato ...................... H04N 5/782 375/240.24 |
| 2004/0257438 A1 * | 12/2004 | Doguchi ............ A61B 1/00009 348/65 |

(Continued)

FOREIGN PATENT DOCUMENTS

| EP | 2 556 790 A1 | 2/2013 |
| EP | 2 636 359 A1 | 9/2013 |

(Continued)

OTHER PUBLICATIONS

Combined Chinese Office Action and Search Report dated Jan. 28, 2019 in corresponding Chinese Patent Application No. 201680027330.7 (with English Translation), 13 pages.

(Continued)

*Primary Examiner* — Joseph G Ustaris
*Assistant Examiner* — Jill D Sechser
(74) *Attorney, Agent, or Firm* — Xsensus LLP

(57) ABSTRACT

A signal processing device includes a first internal module 61 that executes hardware processing, and second internal modules that execute software processing. The first internal module outputs an image signal, division position information indicating division positions, at which a frame of the image signal is divided by a predetermined amount of data, and a timing signal, to the second internal modules, and generates, based on the image signal that has been subjected to the software processing and input from the second internal modules, a video signal for display. Based on the timing signal and the division position information, the second internal modules sequentially execute image processing by the software processing on the image signal per the predetermined amount of data, and sequentially output the image signal per the predetermined amount of data that has been (Continued)

subjected to the image processing, to the first internal module.

11 Claims, 5 Drawing Sheets

(52) U.S. Cl.
CPC ............ *A61B 1/00045* (2013.01); *A61B 1/04* (2013.01); *A61B 1/053* (2013.01)

(56) References Cited

U.S. PATENT DOCUMENTS

| | | | |
|---|---|---|---|
| 2006/0038888 A1* | 2/2006 | Kotouda | H04N 19/60 348/211.14 |
| 2010/0061652 A1 | 3/2010 | Takeshima et al. | |
| 2010/0128116 A1* | 5/2010 | Sato | A61B 1/00045 348/65 |
| 2011/0196201 A1 | 8/2011 | Sato et al. | |
| 2012/0238809 A1 | 9/2012 | Sato et al. | |
| 2013/0041218 A1 | 2/2013 | Iida et al. | |
| 2013/0169775 A1* | 7/2013 | Ono | A61B 1/00009 348/68 |
| 2013/0208101 A1 | 8/2013 | Ono | |
| 2014/0092216 A1* | 4/2014 | Kawata | H04N 5/378 348/45 |
| 2014/0161369 A1 | 6/2014 | Ishihara | |
| 2015/0216400 A1 | 8/2015 | Iida et al. | |
| 2015/0238073 A1* | 8/2015 | Charles | A61B 90/20 600/102 |
| 2016/0066769 A1* | 3/2016 | Hashimoto | A61B 1/00006 600/109 |
| 2017/0105609 A1* | 4/2017 | Nakayama | H04N 19/60 348/211.14 |

FOREIGN PATENT DOCUMENTS

| | | |
|---|---|---|
| EP | 2 745 761 A1 | 6/2014 |
| JP | 2005-189546 A | 7/2005 |
| JP | 2007-50115 A | 3/2007 |
| JP | 2007-319342 A | 12/2007 |
| JP | 2010-68084 A | 3/2010 |
| JP | 5317886 B2 | 10/2013 |
| JP | 2013-235114 A | 11/2013 |

OTHER PUBLICATIONS

International Search Report dated May 24, 2016 in PCT/JP2016/055098 filed Feb. 22, 2016.
Extended European Search Report dated Dec. 25, 2018 in Patent Application No. 16796141.6

* cited by examiner

SIGNAL PROCESSING DEVICE AND MEDICAL OBSERVATION SYSTEM

TECHNICAL FIELD

The present invention relates to: a signal processing device that is connected to a medical observation device, such as an endoscope, and outputs a video signal for display; and a medical observation system including the signal processing device.

BACKGROUND ART

Conventionally, in the medical field, medical observation systems for capturing an image of inside of a subject (in a living body), such as a human, by use of an imaging element, and observing inside the living body, have been known (see, for example, Patent Literature 1).

A medical observation system (electronic endoscopic system) described in Patent Literature 1 includes: an endoscope (electronic endoscope) that captures an image inside a living body and generates an image signal; a signal processing device (processor, or image processing device) that processes the image signal input from the endoscope; and a display device (monitor) that displays thereon a captured image based on a video signal that has been processed by the signal processing device.

The signal processing device includes an image processing circuit, and executes image processing on the image signal by hardware processing.

CITATION LIST

Patent Literature

Patent Literature 1: Japanese Patent No. 5317886

DISCLOSURE OF INVENTION

Technical Problem

In recent years, arithmetic capacity of general-purpose computing on graphics processing units (GPGPU) and the like for executing image processing by software processing has been improving, and modification of a program for executing the image processing is also easy.

Therefore, one may consider incorporating GPGPU and the like also into the signal processing device described in Patent Literature 1. That is, one may consider, as the signal processing device, combining together: a configuration for executing hardware processing (hereinafter, referred to as a hardware module); and a configuration for executing software processing, such as a central processing unit (CPU) or GPGPU (hereinafter referred to as a software module).

As the hardware module, one may consider a configuration that executes, by hardware processing: a process of inputting an image signal from an endoscope and outputting the image signal to the software module; a process of generating and outputting a video signal by format conversion or the like of an output image for the image signal that has been subjected to image processing and input from the software module; and the like.

When the hardware module and the software module are combined together, their times need to be reconciled with each other. A general method considered to reconcile the times is as follows.

The hardware module outputs an image signal input from an endoscope, to the software module.

Every time the software module receives an image signal corresponding to one frame, from the hardware module, the software module executes image processing on the image signal of that frame. Every time image processing on an image signal corresponding to one frame is completed, the software module sequentially outputs the image signal to the hardware module.

The hardware module receives the image signal from the software module, and based on that image signal, generates and outputs a video signal.

That is, the general method considered to reconcile the times between the hardware module and the software module is a method of transferring an image signal for each frame between the hardware module and the software module.

However, when an image signal is transferred between the hardware module and the software module for each frame as described above, there is a problem that latency required for each process is increased. When the latency is large, an image captured by the endoscope is displayed on a display device late by a predetermined number of frames, and the image captured by the endoscope is unable to be promptly displayed on the display device.

In particular, execution time of processing by the software module is unstable. Therefore, a margin needs to be provided for the processing time of the software module. When the software module executes image processing per frame as described above, a vey large margin needs to be set for the processing time of that frame. Therefore, a delay is caused in output of an image signal that has been subjected to image processing from the software module to the hardware module, and the above described latency is even more increased.

The present invention has been made in view of the above, and aims to provide a signal processing device and a medical observation system that enable latency required for each process to be minimized.

Solution to Problem

To solve the above-described problem and achieve the object, a signal processing device according to the present invention is a signal processing device that is connected to a medical observation device that performs an examination inside a subject and outputs an image signal according a result of the examination, and that outputs a video signal for display, and the signal processing device includes: a first internal module configured to execute hardware processing; and a second internal module configured to execute software processing, wherein the first internal module outputs the image signal input from the medical observation device, division position information indicating division positions at which a frame of the image signal is divided by a predetermined amount of data, and a timing signal indicating processing timing of the software processing, to the second internal module, and generates, based on the image signal that has been subjected to the software processing and input from the second internal module, the video signal for display, and the second internal module sequentially executes, based on the timing signal and the division position information, image processing on the image signal per the amount of data, through the software processing, and sequentially outputs the image signal per the amount of data that has been subjected to the image processing, to the first internal module.

Moreover, in the above-described signal processing device according to the present invention, the signal processing device is configured to enable the amount of data to be changed.

Moreover, in the above-described signal processing device according to the present invention, the first internal module includes a storage unit that temporarily stores therein the image signal input from the medical observation device, and the first internal module outputs the image signal stored in the storage unit, the division position information, and the timing signal, to the second internal module.

Moreover, a medical observation system according to the present invention includes: a medical observation device that performs an examination inside a subject and outputs an image signal according to a result of the examination; the above-described signal processing device; and a display device that displays an image based on an imaging signal for display output from the signal processing device.

Advantageous Effects of Invention

A signal processing device according to the present invention includes a first internal module that executes hardware processing, and a second internal module that executes software processing. The first internal module outputs an image signal, division position information, and a timing signal, to the second internal module. Based on the timing signal and the division position information, the second internal module divides a frame of the image signal by a predetermined amount of data, and sequentially executes image processing per that amount of data. The second internal module sequentially outputs the image signal that has been subjected to the image processing per the amount of data, to the first internal module. That is, between the first and second internal modules, the image signal is transferred per the above described predetermined amount of data smaller than one frame.

Therefore, the second internal module is able to immediately start processing if, before receiving the image signal corresponding to one frame, the second internal module receives the predetermined amount of data, by which the one frame is divided, from the first internal module. Further, since a configuration that executes image processing per the predetermined amount of data is adopted, as compared to a configuration that executes image processing per frame, a margin set for the processing time in the second internal module is able to be decreased.

Therefore, the signal processing device according to the present invention has an effect of enabling latency required for each process to be minimized.

A medical observation system according to the present invention includes the above described signal processing device, and thus has the same effects as the above described signal processing device. Further, since latency required for each process is able to be minimized, an image captured by a medical observation device is able to be promptly displayed on a display device.

BEST MODE FOR CARRYING OUT THE INVENTION

Hereinafter, by reference to the drawings, modes for carrying out the present invention (hereinafter, "embodiments") will be described. The present invention is not limited by the embodiments described below. Further, in illustration of the drawings, the same signs are appended to the same portions.

First Embodiment

[Schematic Configuration of Medical Observation System]

Figure 1:
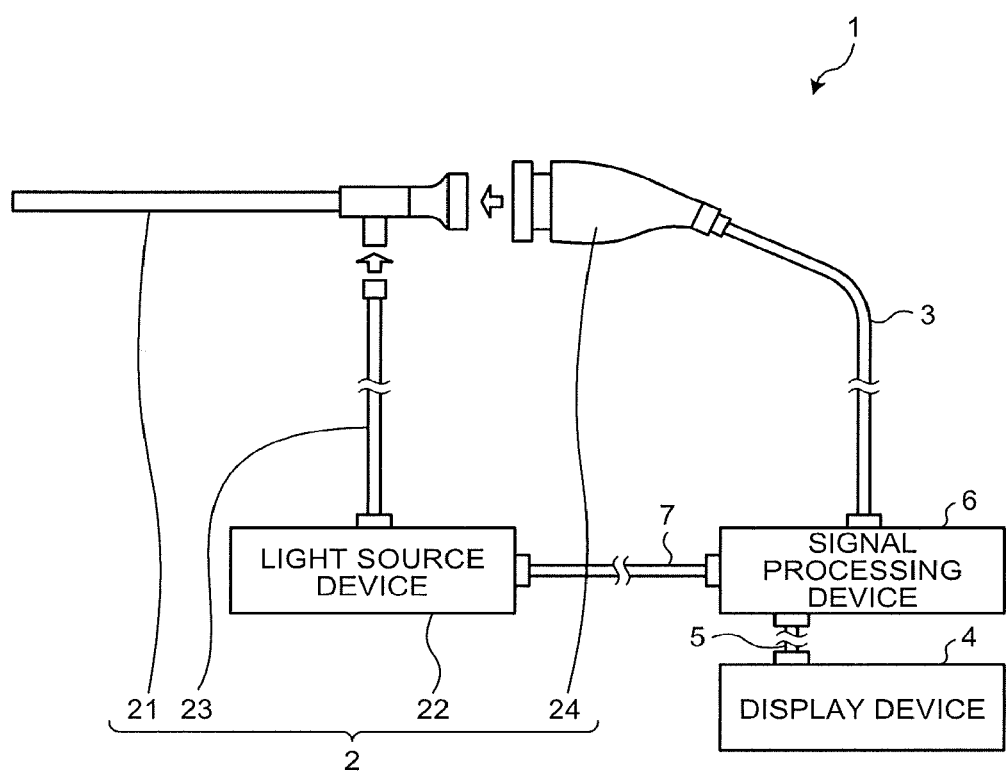
FIG. 1 is a diagram illustrating a schematic configuration of a medical observation system according to a first embodiment of the present invention.

FIG. 1 is a diagram illustrating a schematic configuration of a medical observation system 1 according to a first embodiment of the present invention.

The medical observation system 1 is a system, which is used in the medical field, and is for observing inside of a subject, such as a human (in a living body). This medical observation system 1 includes, as illustrated in FIG. 1, an endoscope 2, a first transmission cable 3, a display device 4, a second transmission cable 5, a signal processing device 6, and a third transmission cable 7.

The endoscope 2 has functions as a medical observation device according to the present invention, and examines inside a living body and outputs a signal according to a result of the examination. This endoscope 2 includes, as illustrated in FIG. 1, an insertion unit 21, a light source device 22, a light guide 23, and a camera head 24.

The insertion unit 21 is rigid, has an elongated shape, and is inserted into a living body. Provided in this insertion unit 21 is an optical system that is formed by use of one lens or plural lenses, and that condenses an object image.

One end of the light guide 23 is connected to the light source device 22, which supplies light for illuminating inside a living body to the one end of the light guide 23 under control by the signal processing device 6.

The one end of the light guide 23 is connected freely attachably to and detachably from the light source device 22, and the other end of the light guide 23 is connected freely attachably to and detachably from the insertion unit 21. The light guide 23 transmits the light supplied from the light source device 22 from the one end thereof to the other end thereof, to supply the light to the insertion unit 21. The light supplied to the insertion unit 21 is emitted from a distal end of the insertion unit 21, and emitted into the living body. The light emitted into the living body (object image) is condensed by the optical system in the insertion unit 21.

The camera head 24 is connected freely attachably to and detachably from a proximal end of the insertion unit 21. Under control by the signal processing device 6, the camera head 24 captures the object image condensed by the insertion unit 21, and outputs an imaging signal resulting from the image capturing (corresponding to "an image signal according to an examination result" according to the present invention).

In this first embodiment, the camera head 24 has only one imaging element (illustration thereof being omitted) for generating the imaging signal. Further, the camera head 24 photoelectrically converts the imaging signal into an optical signal, and outputs the imaging signal as the optical signal.

The first transmission cable 3 has one end connected freely attachably to and detachably from the signal processing device 6, and another end connected freely attachably to and detachably from the camera head 24. Specifically, the first transmission cable 3 is a cable having plural electric wirings (illustration thereof being omitted) and an optical fiber (illustration thereof being omitted), which are arranged inside an outer covering, which is the outermost layer thereof.

The above mentioned plural electric wirings are electric wirings for respectively transmitting a control signal, a timing signal, electric power, and the like, which are output from the signal processing device 6, to the camera head 24.

The above mentioned optical fiber is an optical fiber for transmitting the imaging signal (optical signal) output from the camera head 24 to the signal processing device 6. If the imaging signal is output as an electric signal from the camera head 24, the optical fiber may be changed to an electric wiring.

The display device 4 (for example, a monitor of SD, HD, 4K, or better) displays an image under control by the signal processing device 6.

The second transmission cable 5 (for example, HD-SDI or 3G-SDI, HDMI (registered trademark), DisplayPort (registered trademark), or the like) has one end connected freely attachably to and detachably from the display device 4, and another end connected freely attachably to and detachably from the signal processing device 6. The second transmission cable 5 transmits a video signal processed by the signal processing device 6 to the display device 4.

The signal processing device 6 is configured to include a CPU or the like, and comprehensively controls operation of the light source device 22, the camera head 24, and the display device 4.

The third transmission cable 7 has one end connected freely attachably to and detachably from the light source device 22, and another end connected freely attachably to and detachably from the signal processing device 6. The third transmission cable 7 transmits a control signal from the signal processing device 6 to the light source device 22.

[Configuration of Signal Processing Device]

Next, a configuration of the signal processing device 6 will be described.

Hereinafter, as the signal processing device 6, a processing function for an imaging signal input via the first transmission cable 3 from the camera head 24 will be described mainly.

Figure 2:
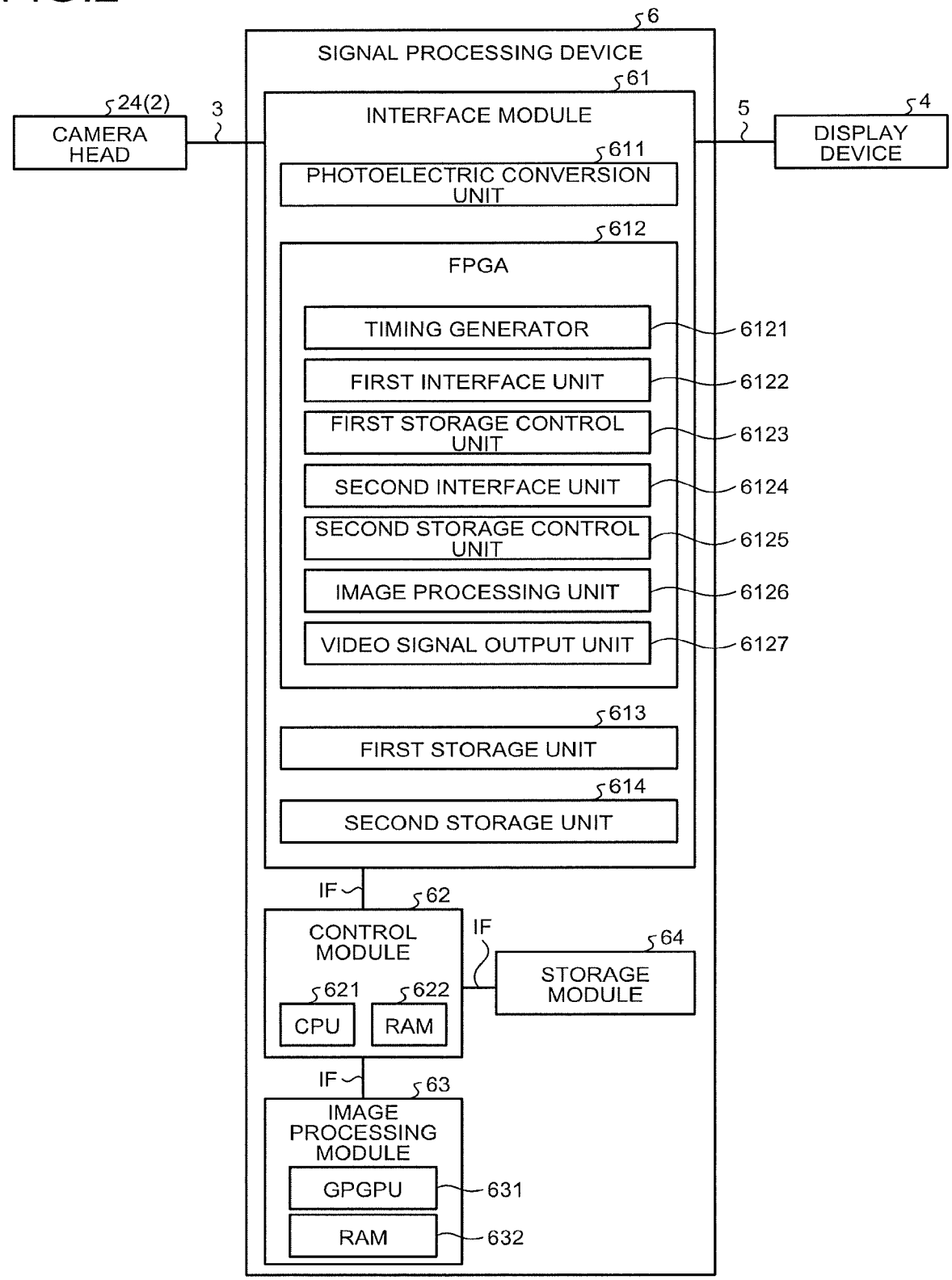
FIG. 2 is a block diagram illustrating a configuration of a signal processing device illustrated in FIG. 1.

FIG. 2 is a block diagram illustrating the configuration of the signal processing device 6.

Omitted from the illustration in FIG. 2 are: a connector enabling the camera head 24 and the first transmission cable 3 to be attached to and detached from each other; a connector enabling the first transmission cable 3 and the signal processing device 6 to be attached to an detached from each other; a connector for enabling the display device 4 and the second transmission cable 5 to be attached to and detached from each other; and a connector enabling the second transmission cable 5 and the signal processing device 6 to be attached to and detached from each other. Further, in FIG. 2, the plural electric wirings and the optical fiber forming the first transmission cable 3 are illustrated as a single cable.

The signal processing device 6 is assembled by utilization of general purpose PC architecture.

Specifically, the signal processing device 6 has, as illustrated in FIG. 2, a configuration, in which an interface module 61, a control module 62, an image processing module 63, and a storage module 64 are connected by use of general purpose interfaces IFs.

Each of these modules 61 to 64 is arranged inside a casing, although specific illustration thereof has been omitted. After assembly, testing, and the like of the signal processing device 6 have been performed, the signal processing device 6 is set in a state, in which inside of the casing is unable to be made open.

The interfaces IFs are interfaces having a communication protocol and a connector shape conforming to a communication interface standard (for example, a standard for PC/AT compatibles).

In this first embodiment, as the interfaces IFs, PCI EXPRESS (registered trademark) (PCIe) is adopted. That is, in this first embodiment, each of the modules 62 to 64 is formed of PC parts conforming to the PCIe standard.

The control module 62 is a module that executes software processing, and has functions as a second internal module according to the present invention. The control module 62 controls operation of the light source device 22, operation of the camera head 24, operation of the display device 4, and operation of the whole signal processing device 6.

In this first embodiment, the control module 62 is formed of a mother board, on which a CPU 621 (FIG. 2), a random access memory (RAM) 622 (FIG. 2), and the like are installed, and which conforms to the standard for PC/AT compatibles. In the mother board, expansion slots for connecting respectively to the interface module 61, the image processing module 63, and the storage module 64 are provided.

The interface module 61 is a module that executes hardware processing, and has functions as a first internal module according to the present invention. The interface module 61 is installed in an expansion slot provided in the control module 62 (a PCIe slot in this embodiment). This interface module 61 includes, as illustrated in FIG. 2, a photoelectric conversion unit 611, a field programmable gate array (FPGA) 612, a first storage unit 613 (corresponding to a storage unit according to the present invention), and a second storage unit 614.

The photoelectric conversion unit 611 photoelectrically converts an imaging signal (optical signal) input from the camera head 24 via the first transmission cable 3, into an electric signal, and outputs the photoelectrically converted imaging signal to the FPGA 612. If the imaging signal is output from the camera head 24 as an electric signal, the photoelectric conversion unit 611 is omitted, and the electric signal is directly input to the FPGA 612.

The FPGA 612 is a logical circuit that has been subjected to configuration by the control module 62. This FPGA 612 includes, as illustrated in FIG. 2, a timing generator 6121, a first interface unit 6122, a first storage control unit 6123, a second interface unit 6124, a second storage control unit 6125, an image processing unit 6126, and a video signal output unit 6127.

The timing generator 6121 generates a timing signal (corresponding to a timing signal according to the present invention) for synchronization among the camera head 24, the interface module 61, the control module 62, and the like.

The first interface unit 6122 converts the imaging signal that has been photoelectrically converted by the photoelectric conversion unit 611 into data that are processable inside the FPGA 612.

The first storage control unit 6123 controls writing and reading of data into and from the first storage unit 613, such as a VRAM. Based on a timing signal generated by the timing generator 6121, the first storage control unit 6123 temporarily stores the data (imaging signal) that have been processed by the first interface unit 6122, into the first storage unit 613, and reads those data from the first storage unit 613.

The second interface unit 6124 converts the data (imaging signal) that have been read out from the first storage unit 613 by the first storage control unit 6123 into a digital signal according to the communication interface standard (the PCIe standard, in this first embodiment). Further, based on a set value (information indicating a predetermined amount of data) stored in a memory (illustration thereof being omitted) inside the FPGA 612, the second interface unit 6124 generates division position information indicating division positions where a frame of the digital signal (imaging signal) is divided by the amount of data (set value). The second interface unit 6124 outputs the digital signal (imaging signal), the division position information, and the timing signal generated by the timing generator 6121, to the control module 62, via the interface IF.

Figure 3:
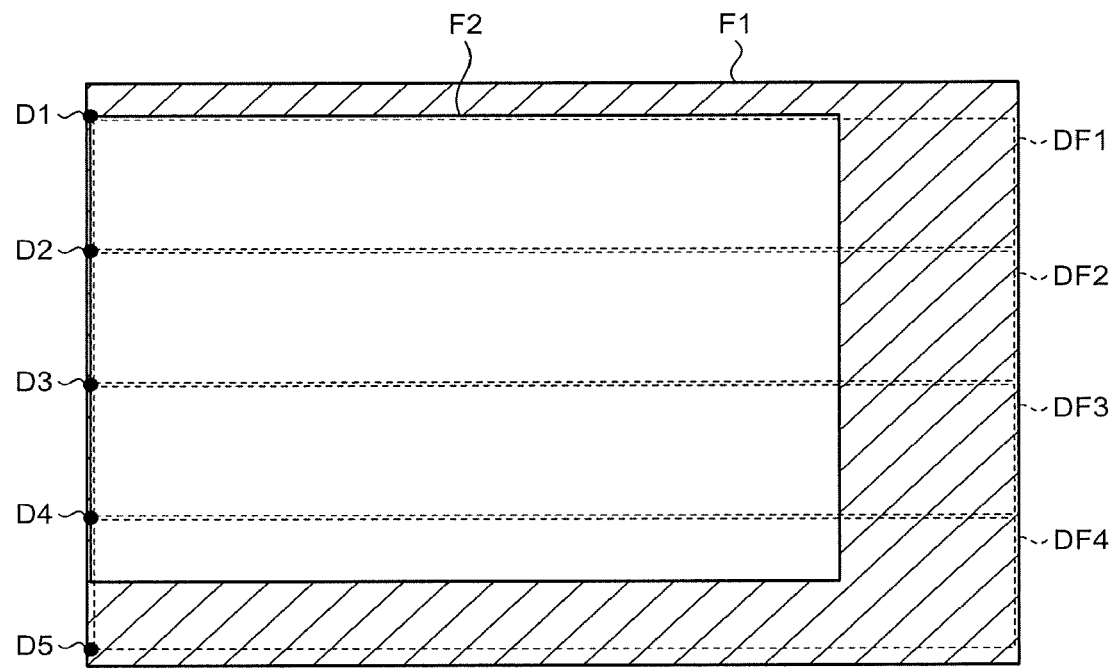
FIG. 3 is a diagram illustrating an example of division position information generated by a second interface unit illustrated in FIG. 2.

FIG. 3 is a diagram illustrating an example of the division position information generated by the second interface unit 6124.

Specifically, in FIG. 3, a larger rectangular frame indicated with a solid line represents an image F1 corresponding to one frame read out from the first storage unit 613 (an image corresponding to one frame of the digital signal (imaging signal) output from the second interface unit 6124 to the control module 62). A smaller rectangular frame indicated with a solid line represents an image F2 corresponding to one frame of data (imaging signal) that have been written into the first storage unit 613 (an image corresponding to one frame captured by the camera head 24). Broken lines represent divided images DF1 to DF4 in a case where division has been performed based on the division position information.

If an image displayed on the display device 4 is 4K, the above mentioned amount of data (set value) has been set at a quarter (560 lines×4400 pixels) of 2240 lines (scanning lines)×4400 pixels (number of pixels).

The image F2 corresponding to the one frame captured by the camera head 24 may be unable to be divided into four by the above mentioned amount of data (560 lines×4400 pixels). Therefore, in this first embodiment, as illustrated in FIG. 3, a configuration is adopted, in which a dummy area (a hatched area in FIG. 3) is added to the image F2, and the division position information is generated based on the image F1 having an image size larger than that of the image F2.

Specifically, the second interface unit 6124 generates, as the division position information in the image F1: a scan start position D1 at the 1st line of the image F2; a scan start position D2 at the 560th line from the 1st line; a scan start position D3 at the 1120th line from the 1st line; a scan start position D4 at the 1680th line from the 1st line; and a scan start position D5 at the 2240th line from the 1st line.

Every time a divided image (in the example of FIG. 3, the divided images DF1 to DF4) is sequentially written into the RAM 622, the control module 62 sequentially outputs the divided image to the image processing module 63, the divided image resulting from division, per frame, of the frame by a predetermined amount of data (in the example of FIG. 3, at each of the scan start positions D1 to D5) based on the division position information input from the second interface unit 6124. Further, the image processing module 63 sequentially executes image processing for each of the divided images input from the control module 62, and sequentially outputs the divided images that have been subjected to the image processing, to the control module 62 via the interface IF.

A configuration may be adopted, in which, upon the output of the divided images from the control module 62 to the image processing module 63, for example, in consideration of the image processing in the image processing module 63 (so that image processing on outer edge portions of the divided images DF1 to DF4 is able to be executed appropriately), a predetermined number of lines (scanning lines) are added to each of upper and lower portions of the divided images DF1 to DF4 in FIG. 3, and the divided images that have been subjected to this addition are output to the image processing module 63.

Hereinafter, the above described processing in the second interface unit 6124, the control module 62, and the image processing module 63 will be referred to as pipeline processing.

In this first embodiment, the FPGA 612 is able to change the above described amount of data (set value). For example, the FPGA 612 changes the amount of data (set value) according to the following states.

When a type of the camera head 24 connected to the signal processing device 6 is different, the amount of data corresponding to one frame of an imaging signal output from the camera head 24 may be different. Further, when a mode of the medical observation system 1 (for example, a high sensitivity mode) is different, output timing of an imaging signal output from the camera head 24 may be different.

Therefore, in order to optimize the pipeline processing (minimize the latency), the FPGA 612 changes, as appropriate, the above described amount of data (set value) according to the type of the camera head 24 connected or the mode of the medical observation system 1.

The second storage control unit 6125 controls writing and reading of data into and from the second storage unit 614, such as a VRAM. Based on a timing signal generated by the timing generator 6121; via the interface IF, the second storage control unit 6125 temporarily stores, into the second storage unit 614, the divided images that have been subjected to the image processing by the image processing module 63 and that have been sequentially received via the control module 62, the interface IF, and the second interface unit 6124 (in the example of FIG. 3, the divided images respectively resulting from image processing on the divided images DF1 to DF4), and reads data that have been stored in the second storage unit 614 per frame.

The image processing unit 6126 executes various types of image processing on the data read out from the second storage unit 614 by the second storage control unit 6125.

Examples of the various types of image processing executed by the image processing unit 6126 include: on-screen display (OSD) processing; processing, in which the captured image based on the data read out from the second storage unit 614 is placed alongside, or superimposed on, an examination image obtained beforehand in another examination, such as MRI, for the same subject; and the like.

The video signal output unit 6127 generates a video signal for display by executing format conversion or the like of an output image for the data that have been processed by the image processing unit 6126, and outputs the video signal to the display device 4 via the second transmission cable 5. When the display device 4 receives the video signal, the display device 4 displays a captured image based on the video signal.

The image processing module 63 is a module that executes software processing, and has functions as a second internal module according to the present invention. The image processing module 63 includes, for example, a GPGPU 631 (FIG. 2), a RAM 632 (FIG. 2), and the like, and is installed in an expansion slot provided in the control module 62 (a PCIe slot in this first embodiment).

Specifically, the image processing module 63 executes, for each of the divided images (in the example of FIG. 3, the divided images DF1 to DF4) input from the control module 62, various types of image processing, such as development processing, noise reduction, color correction, color enhancement, and contour enhancement. The image processing module 63 sequentially outputs the divided images that have been subjected to the various types of image processing, via the interface IF, to the control module 62.

Although specific illustration has been omitted, in the example of FIG. 3 (when the image displayed on the display device 4 is 4K), the image processing module 63 generates divided images, each of which has 540 lines×4096 pixels, by executing the above described various types of image processing on the divided images DF1 to DF4.

The storage module 64 is formed of, for example a solid state drive (SSD), a hard disk drive (HDD), or a dual inline memory module (DIMM), and is installed in an expansion slot provided in the control module 62 (an IDE/SATA connector and a memory socket in this first embodiment).

Specifically, stored in the storage module 64 are a program and an OS (for example, Windows (registered trademark), Linux (registered trademark), Android (registered trademark), iOS (registered trademark), RIOS, or the like), for causing the image processing module 63 to execute the above described various types of image processing.

[Pipeline Processing]

Next, the pipeline processing in the signal processing device 6 (the second interface unit 6124, the control module 62, and the image processing module 63) will be described while reference is made to FIG. 4.

Figure 4:
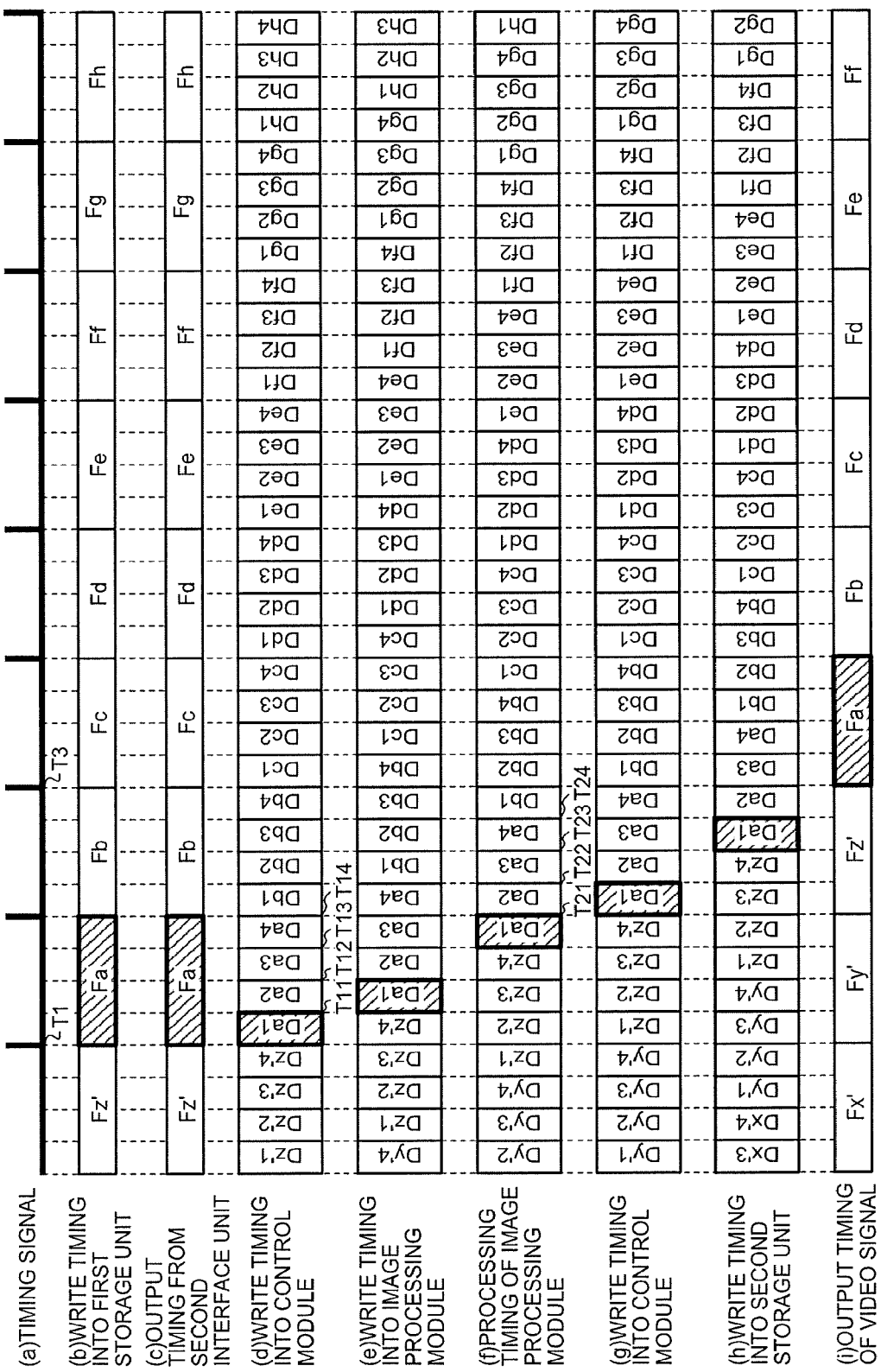
FIG. 4 is a time chart illustrating pipeline processing in the signal processing device illustrated in FIG. 1 and FIG. 2.

FIG. 4 is a time chart illustrating the pipeline processing by the signal processing device 6.

Specifically, FIG. 4(*a*) illustrates a timing signal generated by the timing generator 6121. FIG. 4(*b*) illustrates timings, at which output is made from the camera head 24, and data (imaging signals) are written into the first storage unit 613. FIG. 4(*c*) illustrates output timings, at which data (imaging signals) are read out from the first storage unit 613, and digital signals that are output from the second interface unit 6124 and that are according to the communication interface standard (in this first embodiment, the PCIe standard) are output. FIG. 4(*d*) illustrates timings, at which output is made from the second interface unit 6124, and digital signals (divided images) are written into the RAM 622 of the control module 62. FIG. 4(*e*) illustrates timings, at which reading from the RAM 622 of the control module 62 is executed, and the divided images are written into the RAM 632 of the image processing module 63. FIG. 4(*f*) illustrates processing timings for the image processing in the image processing module 63. FIG. 4(*g*) illustrates timings, at which reading from the RAM 632 of the image processing module 63 is executed, and the divided images that have been subjected to the image processing in the image processing module 63 are written into the RAM 622 of the control module 62. FIG. 4(*h*) illustrates timings, at which reading from the RAM 622 of the control module 62 is executed, and the divided images that have been subjected to the image processing in the image processing module 63 are written into the second storage unit 614. FIG. 4(*i*) illustrates output timings for video signals read out from the second storage unit 614 and output via the image processing unit 6126 and the video signal output unit 6127.

In FIG. 4, for convenience of explanation, since latency required for each process inside the interface module 61 having a hardware configuration is comparatively small, illustration is made as if there is no latency. Further, similarly, illustration is made as if there is no latency between the camera head 24 and the interface module 61, either. Furthermore, in FIG. 4, for identification of the respective frames, characters, "Fa" to "Fh", are appended to portions corresponding to the respective frames. Moreover, to portions corresponding to frames before the frame Fa, characters, "Fx'" to "Fz'", are appended. In addition, for identification of the respective divided images for each frame; for the frame Fa, to portions corresponding to the respective divided images, characters, "Da1 to Da4", are appended. For the other frames Fb to Fh and Fx' to Fz' also, similarly, to portions corresponding to the respective divided images, characters, "Db1 to Db4", "Dc1 to Dc4", "Dd1 to Dd4", "De1 to De4", "Df1 to Df4", "Dg1 to Dg4", "Dh1 to Dh4", "Dx'1 to Dx'4", "Dy'1 to Dy'4", and "Dz'1 to Dz'4", are respectively appended.

Hereinafter, the pipeline processing will be described with a focus on the frame Fa (the divided images Da1 to Da4).

The camera head 24 has been synchronized with the signal processing device 6 by a timing signal generated by the timing generator 6121. Therefore, at a timing T1 (FIG. 4(*a*)) based on the timing signal, as illustrated in FIG. 4(*b*), output of an imaging signal (optical signal) of the frame Fa from the camera head 24 is started.

At that timing T1, as illustrated in FIG. 4(*b*), writing of data (corresponding to the image F2 in the example of FIG. 3) of the frame Fa according to the imaging signal (optical signal) into the first storage unit 613 by the first storage control unit 6123 is started.

Next, at the timing T1, as illustrated in FIG. 4(*c*), reading of data (corresponding to the image F1 in the example of FIG. 3) of the frame Fa from the first storage unit 613 by the first storage control unit 6123 is started, and output of a digital signal (corresponding to the image F1 in the example of FIG. 3) according to the communication interface standard (in this first embodiment, the PCIe standard) and division position information of the frame Fa, from the second interface unit 6124 is started.

From the timing T1, as illustrated in FIG. 4(*d*), the divided images Da1 to Da4 (corresponding to the divided images DF1 to DF4 in the example of FIG. 3) according to the digital signal of the frame Fa are sequentially written into the RAM 622 of the control module 62.

Next, at respective timings T11 to T14 (FIG. 4(*d*)), at which the writing of the divided images Da1 to Da4 into the RAM 622 is completed, the control module 62 starts reading the divided images Da1 to Da4 respectively. That is, every time writing of one divided image is completed, the control module 62 starts reading that divided image.

The image processing module 63 respectively starts, as illustrated in FIG. 4(*e*), writing of the divided images Da1 to Da4 at the respective timings T11 to T14.

Next, the image processing module 63 sequentially starts, as illustrated in FIG. 4(*f*), the various types of image processing on the divided images Da1 to Da4, from, instead of the timing T12, at which writing of the divided image Da1 into the RAM 632 is completed, the timing T13 next to that timing T12, in order to be able to deal with a case, in which the processing in the control module 62 is delayed.

Next, at respective timings T21 to T24 (FIG. 4(*f*)), at which the various types of image processing on the divide images Da1 to Da4 are completed, the image processing module 63 respectively starts reading the divided images Da1 to Da4 that have been subjected to the image processing, from the RAM 632.

The control module 62 then respectively starts, as illustrated in FIG. 4(*g*), writing the divided images Da1 to Da4 that have been subjected to the image processing into the RAM 622, at the respective timings T21 to T24.

Next, the control module 62 starts reading the divided images Da1 to Da4 that have been subjected to the image processing from the RAM 632, from, instead of the timing T22, at which writing of the divided image Da1 that has been subjected to the image processing into the RAM 632 is completed, the timing T23 next to that timing T22, in order to be able to deal with a case, in which the processing in the image processing module 63 is delayed.

From the timing T23, as illustrated in FIG. 4(*h*), writing of the divided images Da1 to Da4 that have been subjected to the image processing, into the second storage unit 614, is started by the second storage control unit 6125.

Next, reading of data of the frame Fa (the divided images Da1 to Da4 that have been subjected to the image processing) from the second storage unit 614 is started by the second storage control unit 6125 at, instead of the timing T24, at which the writing of the divided image Da1 that has been subjected to the image processing into the second storage unit 614 is completed, the timing T3 (FIG. 4(*a*)) that is after the timing T24 and that is based on the timing signal.

The video signal output unit 6127 then starts, as illustrated in FIG. 4(*i*), outputting a video signal according to data of the frame Fa at that timing T3. That is, a captured image according to the data of the frame Fa is displayed on the display device 4 at the timing T3 (which is, in the example of FIG. 4, two frames later than the timing T1, at which the output of the imaging signal for the frame Fa from the camera head 24 is started).

The above described signal processing device 6 according to this first embodiment includes the interface module 61 that executes hardware processing, and the control module 62 and the image processing module 63 that execute software processing. The interface module 61 outputs a digital signal (imaging signal) according to the communication interface standard (the PCIe standard in this first embodiment), division position information, and a timing signal, to the control module 62. Every time a divided image resulting from division of a frame of the digital signal (imaging signal) by a predetermined amount of data (set value) is sequentially written into the RAM 622 based on the timing signal and the division position information, the control module 62 sequentially outputs the divided image to the image processing module 63. Further, the image processing module 63 sequentially executes image processing for each of the divided images. The divided images that have been subjected to the image processing are sequentially output to the interface module 61 via the control module 62. That is, the digital signal (imaging signal) is transferred per divided image smaller than one frame, and pipeline processing is executed; between the interface module 61, and the control module 62 and image processing module 63.

Therefore, the image processing module 63 is able to immediately start image processing when a divided image corresponding to the predetermined amount data (set value) is input, before one frame of the digital signal (imaging signal) is input from the control module 62. Further, since the configuration, in which image processing is executed per divided image, is adopted, as compared to a configuration, in which image processing is executed per frame, a margin set for the processing time of the image processing module 63 is able to be decreased.

Therefore, the signal processing device 6 according to this first embodiment has an effect of enabling latency required for each process to be minimized. Further, the medical observation system 1 according to this first embodiment, in which the signal processing device 6 that enables minimization of the latency has been incorporated, has an effect of enabling an image captured by the endoscope 2 to be promptly displayed on the display device 4.

Further, the signal processing device 6 according to this first embodiment is configured to be able to change the amount of data (set value), by which one frame is divided.

Therefore, the pipeline processing is able to be optimized (latency is able to be minimized) by the amount of data (set value) being changed as appropriate, according to, for example, the type of the camera head 24 connected, or the mode of the medical observation system 1 (for example, the high sensitivity mode, or the like).

Further, the signal processing device 6 according to this first embodiment includes the first storage unit 613 that temporarily stores therein data (imaging signal) that have been output from the camera head 24 and processed by the photoelectric conversion unit 611 and the first interface unit 6122.

Therefore, even if an image corresponding to one frame captured by the camera head 24 (corresponding to the image F2 in the example of FIG. 3) is unable to be divided appropriately by the predetermined amount of data (set value), a dummy area is able to be added to the image so as to enable appropriate division thereof. Therefore, the pipeline processing is able to be executed suitably.

Second Embodiment

Next, a second embodiment of the present invention will be described.

In the following description, to configurations that are the same as those of the above described first embodiment, the same signs will be appended, and detailed description thereof will be omitted or simplified.

In the above described medical observation system 1 according to the first embodiment, only one imaging element is provided in the camera head 24.

In contrast, a medical observation system according to this second embodiment is formed of, for example, a surgical microscope, and enables inside of a subject, such as a human (in a living body), to be displayed as a three dimensional image. Therefore, in the medical observation system according to this second embodiment, a camera head includes two imaging elements that generate two imaging signals having a parallax from each other.

Hereinafter, a configuration of a signal processing device used in the medical observation system according to this second embodiment will be described.

[Configuration of Signal Processing Device]

Figure 5:
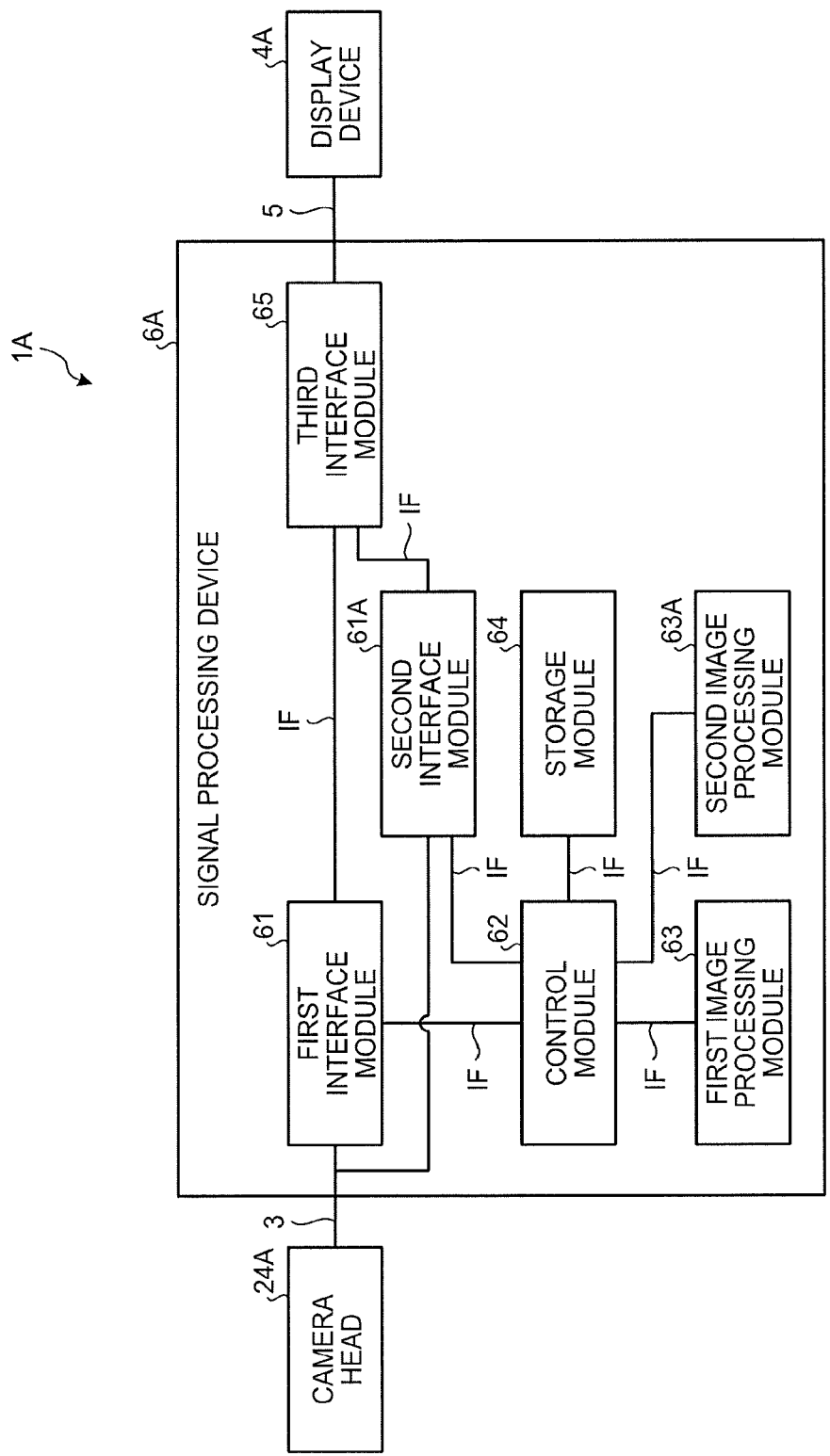
FIG. 5 is a block diagram illustrating a configuration of a signal processing device used in a medical observation system according to a second embodiment of the present invention.

FIG. 5 is a block diagram illustrating a configuration of a signal processing device 6A used in a medical observation system 1A according to the second embodiment of the present invention.

Similarly to FIG. 2, in FIG. 5: omitted from the illustration are: a connector enabling a camera head 24A and the first transmission cable 3 to be attached to and detached from each other; a connector enabling the first transmission cable 3 and the signal processing device 6A to be attached to an detached from each other; a connector for enabling a display device 4A and the second transmission cable 5 to be attached to and detached from each other; and a connector enabling the second transmission cable 5 and the signal processing device 6A to be attached to and detached from each other; and the plural electric wirings and the optical fiber forming the first transmission cable 3 are illustrated as a single cable.

In the signal processing device 6A used in the medical observation system 1A according to this second embodiment, as illustrated in FIG. 5, as compared to the signal processing device 6 (FIG. 2) explained in the above described first embodiment, a second interface module 61A, a second image processing module 63A, and a third interface module 65 have been added as internal modules installed in expansion slots (PCIe slots or the like) provided in the control module 62.

Hereinafter, in order to distinguish the interface module 61 and the image processing module 63 explained in the above described first embodiment, from the second interface module 61A and the second image processing module 63A; the interface module 61 and the image processing module 63 will respectively be referred to as the first interface module 61 and the first image processing module 63.

The second interface module 61A has been added in association with the provision of the two imaging elements in the camera head 24A (FIG. 5) according to this second embodiment (addition of one imaging element to the camera head 24 explained in the above described first embodiment), and has functions similar to those of the first interface module 61.

That is, the first interface module 61 executes processing on an imaging signal generated by one imaging element of the two imaging elements. On the contrary, the second interface module 61A executes processing on an imaging signal generated by the other imaging element.

In this second embodiment, the first interface module 61 outputs a video signal, as illustrated in FIG. 5, to the third interface module 65 via an interface IF, instead of to a display device 4A. The same applies to the second interface module 61A.

The second image processing module 63A has been added in association with the provision of the two imaging elements in the camera head 24A, and has functions similar to those of the first image processing module 63.

That is, the first image processing module 63 executes processing on a digital signal (imaging signal) generated by the one imaging element of the two imaging elements and input from the first interface module 61 via interfaces IFs and the control module 62. On the contrary, the second image processing module 63A executes processing on a digital signal (imaging signal) generated by the other imaging element and input from the second interface module 61A via interfaces IFs and the control module 62.

The third interface module 65 respectively receive video signals from the first and second interface modules 61 and 61A via interfaces IFs, and generates a three dimensional video signal for three dimensional image display by executing predetermined signal processing on each of the video signals. The third interface module 65 outputs the generated three dimensional video signals to the display device 4A via the second transmission cable 5.

The display device 4A is formed of a 3D display of, for example, the integral imaging type, or the multi-eye type. The display device 4A displays thereon a three dimensional image based on the three dimensional video signal input via the second transmission cable 5.

Even if the medical observation system 1A is configured as described in the above described second embodiment, effects similar to those of the above first embodiment are achieved.

Other Embodiments

Thus far, modes for carrying out the present invention have been described, but the present invention is not to be limited only by the above described embodiments.

In the above described first embodiment, the endoscope (rigid endoscope) using a rigid mirror (insertion unit 21) is adopted as the medical observation device according to the present invention, but not being limited thereto, a flexible endoscope using a flexible mirror (illustration thereof being omitted) may be adopted instead. Further, as the medical observation device according to the present invention, not being limited to the rigid endoscope or the flexible endoscope, an ultrasonic endoscope using an ultrasonic examination probe, or the like, may be adopted instead.

In the above described first and second embodiments, PCIe is adopted as the interfaces IFs, but, not being limited to PCIe, as long as they are interfaces according to the communication interface standard (for example, conforming to the standard for PC/AT compatibles); USB, Ethernet (registered trademark), serial ATA, HDMI (registered trademark), IEEE 1394 (registered trademark), DisplayPort (registered trademark), RS232C, general purpose input/output (GPIO), or the like may be adopted instead.

In the above described first and second embodiments, divided images resulting from division of one frame into four have been described as an example, but the division number is not limited to this example, and the division may be made into two, eight, sixteen, or the like. Further, in the above described first and second embodiments, as illustrated in FIG. 3, the division is executed by the number of lines (the number of scanning lines), but not being limited thereto, as long as the division is made by a predetermined amount of data (set value), a divided portion may be in the middle of a scanning line.

In the above described first embodiment, the signal processing device 6 includes only one image processing module 63, but the number thereof is not limited to one, and may be two like in the above described second embodiment, or may be three or more.

REFERENCE SIGNS LIST 1, 1A MEDICAL OBSERVATION SYSTEM
2 ENDOSCOPE
3 FIRST TRANSMISSION CABLE
4, 4A DISPLAY DEVICE
5 SECOND TRANSMISSION CABLE
6, 6A SIGNAL PROCESSING DEVICE
7 THIRD TRANSMISSION CABLE
21 INSERTION UNIT
22 LIGHT SOURCE DEVICE
23 LIGHT GUIDE 24, 24A CAMERA HEAD
61 INTERFACE MODULE (FIRST INTERFACE MODULE)
61A SECOND INTERFACE MODULE
62 CONTROL MODULE
63 IMAGE PROCESSING MODULE (FIRST IMAGE PROCESSING MODULE)
63A SECOND IMAGE PROCESSING MODULE
64 STORAGE MODULE
65 THIRD INTERFACE MODULE
611 PHOTOELECTRIC CONVERSION UNIT
612 FPGA
613 FIRST STORAGE UNIT
614 SECOND STORAGE UNIT
621 CPU
622 RAM
631 GPGPU
632 RAM
6121 TIMING GENERATOR
6122 FIRST INTERFACE UNIT
6123 FIRST STORAGE CONTROL UNIT
6124 SECOND INTERFACE UNIT
6125 SECOND STORAGE CONTROL UNIT
6126 IMAGE PROCESSING UNIT
6127 VIDEO SIGNAL OUTPUT UNIT
DF1 TO DF4 DIVIDED IMAGE
F1, F2 IMAGE
IF INTERFACE

The invention claimed is:

1. A signal processing device that is connected to a medical observation device that performs an examination inside a subject and outputs an image signal including a plurality of frames output sequentially according to a result of the examination, and that outputs a video signal for display, the signal processing device comprising:
first internal circuitry configured to execute hardware processing; and
second internal circuitry configured to execute software processing, wherein
the first internal circuitry outputs the image signal input from the medical observation device, division position information indicating division positions at which a frame of the image signal is divided by a predetermined amount of data into a plurality of sub-frames, and a timing signal indicating processing timing of the software processing to be performed sequentially on each of the plurality of sub-frames, to the second internal circuitry, and generates, based on the image signal that has been subjected to the software processing and input from the second internal circuitry, the video signal for display, the predetermined amount of data at which the frame of the image signal is divided into the plurality of sub-frames being set based on a type of camera connected to the medical observation device, and
the second internal circuitry sequentially executes, based on the timing signal and the division position information, image processing on each sub-frame in the plurality of sub-frames in the image signal per the predetermined amount of data, through the software processing, and sequentially outputs each sub-frame in the plurality of sub-frames of each frame in the image signal per the predetermined amount of data that has been subjected to the image processing, to the first internal circuitry.

2. The signal processing device according to claim 1, wherein the signal processing device is configured to enable the amount of data to be changed.

3. The signal processing device according to claim 1, wherein the first internal circuitry includes a storage that temporarily stores therein the image signal input from the medical observation device, and the first internal circuitry outputs the image signal stored in the storage, the division position information, and the timing signal, to the second internal circuitry.

4. The signal processing device according to claim 1, wherein:
the first internal circuitry includes a first standard interface;
the second internal circuitry includes a second standard interface;
each of the first and second standard interface includes a communication protocol and a connector shape conforming to a communication interface standard;
the first internal circuitry outputs the image signal via the first standard interface; and
the second internal circuitry sequentially outputs the image signal via the second standard interface.

5. The signal processing device according to claim 1, wherein when the image signal corresponds to an image that is smaller than a predetermined image size, dummy data is added to the image signal to obtain an image signal corresponding to an image having the predetermined size.

6. A medical observation system, comprising:
a medical observation device that performs an examination inside a subject and outputs an image signal according to a result of the examination; and
the signal processing device according to claim 1.

7. A method of operating a signal processing device that is connected to a medical observation device that performs an examination inside a subject and outputs an image signal including a plurality of frames output sequentially according to a result of the examination, and that outputs a video signal for display, the method comprising:
executing, in first internal circuitry, hardware processing;
executing, in second internal circuitry, software processing;
outputting, by the first internal circuitry, the image signal input from the medical observation device, division position information indicating division positions at which a frame of the image signal is divided by a predetermined amount of data into a plurality of sub-frames, and a timing signal indicating processing timing of the software processing to be performed sequentially on each of the plurality of sub-frames, to the second internal circuitry;
generating, based on the image signal that has been subjected to the software processing and input from the second internal circuitry, the video signal for display, the predetermined amount of data at which the frame of the image signal is divided into the plurality of sub-frames being set based on a type of camera connected to the medical observation device; and
sequentially executing, by the second internal circuitry, based on the timing signal and the division position information, image processing on each sub-frame in the plurality of sub-frames in the image signal per the predetermined amount of data, through the software processing, and sequentially outputting each sub-frame in the plurality of sub-frames of each frame in the image signal per the predetermined amount of data that has been subjected to the image processing, to the first internal circuitry.

8. The method according to claim 7, further comprising: enabling the amount of data to be changed.

9. The method according to claim 7, further comprising:
- temporarily storing, in a storage of the first internal circuitry, the image signal input from the medical observation device; and
- outputting, from the first internal circuitry, the image signal stored in the storage, the division position information, and the timing signal, to the second internal circuitry.

10. The method according to claim 7, wherein the first internal circuitry includes a first standard interface, the second internal circuitry includes a second standard interface, each of the first and second standard interface includes a communication protocol and a connector shape conforming to a communication interface standard, and the method further comprises:
- outputting the image signal via the first standard interface; and
- sequentially outputting the image signal via the second standard interface.

11. The method according to claim 7, wherein when the image signal corresponds to an image that is smaller than a predetermined image size, the method further comprising:
- adding dummy data to the image signal to obtain an image signal corresponding to an image having the predetermined size.

* * * * *